(12) United States Patent
Takase

(10) Patent No.: US 9,456,487 B2
(45) Date of Patent: Sep. 27, 2016

(54) HIGH-FREQUENCY CONTROL DEVICE FOR ACCELERATOR AND PARTICLE BEAM THERAPY SYSTEM

(75) Inventor: Hidenobu Takase, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 54 days.

(21) Appl. No.: 14/395,385

(22) PCT Filed: Jul. 24, 2012

(86) PCT No.: PCT/JP2012/068665
§ 371 (c)(1),
(2), (4) Date: Oct. 17, 2014

(87) PCT Pub. No.: WO2014/016896
PCT Pub. Date: Jan. 30, 2014

(65) Prior Publication Data
US 2015/0073199 A1 Mar. 12, 2015

(51) Int. Cl.
*H05H 7/02* (2006.01)
*A61N 5/10* (2006.01)
(Continued)

(52) U.S. Cl.
CPC .............. *H05H 7/02* (2013.01); *A61N 5/1043* (2013.01); *A61N 5/1048* (2013.01);
(Continued)

(58) Field of Classification Search
CPC .... H05H 7/02; H05H 13/04; H05H 2277/11; A61N 5/1043; A61N 5/1048; A61N 5/1077; A61N 2005/1074; A61N 2005/1087; G21K 5/04
See application file for complete search history.

(56) References Cited

U.S. PATENT DOCUMENTS

| 4,870,287 A * | 9/1989 | Cole ........................ A61N 5/10 250/398 |
| 6,822,244 B2 * | 11/2004 | Beloussov ............... A61N 5/10 250/492.1 |

(Continued)

FOREIGN PATENT DOCUMENTS

| JP | 2000-232000 A | 8/2000 |
| JP | 2006-128087 A | 5/2006 |

(Continued)

OTHER PUBLICATIONS

Office Action issued on Jan. 16, 2015, by the Taiwanese Patent Office in corresponding Taiwanese Patent Application No. 101136183, and an English translation of the Office Action. (6 pages).

(Continued)

*Primary Examiner* — Jack Berman
(74) *Attorney, Agent, or Firm* — Buchanan Ingersoll & Rooney PC

(57) ABSTRACT

A hard disk drive memory which stores pattern data of a high-frequency to be applied for each combination of energy and intensity of the generated particle beam and a local memory, which reads a plurality of pattern data of a high-frequency for each patient together with a sequential order of changing energy and intensity from the hard disk drive memory and stores data in order to perform a scanning irradiation method in which a layered particle beam irradiation region in a depth direction of an affected part of the patient is formed sequentially by changing energy and intensity of the particle beam sequentially to irradiate an affected part of a patient which is an irradiation subject with the particle beam, and which reads out data faster than the hard disk drive memory are provided.

2 Claims, 9 Drawing Sheets

(51) Int. Cl.
*H05H 13/04* (2006.01)
*G21K 5/04* (2006.01)

(52) U.S. Cl.
CPC ............. *A61N 5/1077* (2013.01); *G21K 5/04* (2013.01); *H05H 13/04* (2013.01); *A61N 2005/1087* (2013.01); *H05H 2277/11* (2013.01)

(56) References Cited

U.S. PATENT DOCUMENTS

| | | |
|---|---|---|
| 2006/0076515 A1 | 4/2006 | Matsuda et al. |
| 2010/0171447 A1 | 7/2010 | Balakin |
| 2011/0073778 A1 | 3/2011 | Natori et al. |

FOREIGN PATENT DOCUMENTS

| | | |
|---|---|---|
| JP | 2010-003538 A | 1/2010 |
| JP | 2011-072537 A | 4/2011 |

OTHER PUBLICATIONS

International Search Report (PCT/ISA/210) mailed on Aug. 21, 2012, by the Japanese Patent Office as the International Searching Authority for International Application No. PTC/JP2012/068665.

Extended European Search Report mailed Feb. 16, 2016 by the EPO in corresponding International Patent Application No. PCT/JP2012/068665 (7 pages).

\* cited by examiner

| OPERATION SEQUENTIAL ORDER | ENERGY | INTENSITY |
|---|---|---|
| 1 | 400MeV | 3 |
| 2 | 380MeV | 3 |
| 3 | 350MeV | 4 |
| 4 | 310MeV | 4 |
| 5 | 290MeV | 2 |
| 6 | 270MeV | 1 |

FIG. 4

HIGH-FREQUENCY CONTROL DEVICE FOR ACCELERATOR AND PARTICLE BEAM THERAPY SYSTEM

TECHNICAL FIELD

This invention relates to a high-frequency control device for an accelerator such as a synchrotron which is a radiation source for a particle beam therapy system and a particle beam therapy system.

BACKGROUND ART

A particle beam therapy is performed by irradiating affected tissue with a particle beam so as for the affected tissue to be damaged, and is one of radiation therapy in a broad sense. Regarding a particle beam such as a proton, a heavy ion beam, etc., unlike other radiation such as γ-ray, X-ray, a depth range of applying dose can be adjusted by energy of a particle beam, dose can be applied according to a three-dimensional shape of an affected part. Therefore, especially, it is required for an accelerator for a particle beam therapy system to supply a particle beam having accurate energy and orbit.

An accelerator comprises deflection electromagnets for forming an orbit, an acceleration cavity for accelerating a particle beam using a high-frequency, and vacuum ducts which are passages for a particle beam to pass through, etc. Magnetic fields of the deflection electromagnets change according to predetermined patterns with acceleration of a particle beam (energy growth). At the same time, an orbit frequency of a particle beam changes. Therefore, in order to accelerate a particle beam stably, it is necessary to control a frequency or amplitude (intensity) of a high-frequency signal, which is applied to the acceleration cavity, according to a predetermined pattern.

In order to simplify the above-mentioned control, for example, a RF control device, by which a frequency reference signal of a high-frequency signal which is made by a computer in advance is stored and is sequentially read out during operation is proposed (for example, refer to Patent Document 1). However, according to the above-mentioned system, data volume is vast and data conditioning is not easy and number of components is also great. Therefore, a high-frequency control device, wherein an operation pattern of an accelerator is divided into a flat stable region and a region having a flat acceleration part, and a wave-form data of each region is used to control is proposed (for example, refer to Patent Document 2).

On the other hand, an irradiation method of a particle beam therapy is broadly divided into a broad irradiation method in which whole of an affected part of a patient which is an irradiation subject is irradiated simultaneously with a particle beam and a scanning irradiation method in which a particle beam is scanned to irradiate. In a case of a broad irradiation method, a particle beam to be irradiated has definite energy. On the other hand, in a case of a scanning irradiation method, energy of a particle beam is changed so as to irradiate a wide range of depth direction. Energy of a particle beam is changed by changing a magnetic field of an accelerator and a pattern of a high-frequency. Therefore, in a case of a scanning irradiation method, it is necessary to set an operation pattern of an accelerator in accordance with energy and intensity for each energy and intensity. Consequently, in comparison with a broad irradiation method, it is necessary to store more operation patterns.

PRIOR ART REFERENCE

Patent Document

[Patent Document 1]
Japanese Patent Application Laid-Open No. 2000-232000 (Paragraph 0031-0050, FIG. 1)
[Patent Document 2]
Japanese Patent Application Laid-Open No. 2010-3538 (Paragraph 0018-0024, FIG. 2-FIG. 5)

DISCLOSURE OF THE INVENTION

Problems to be Solved by the Invention

Regarding a scanning irradiation method, in order for a high-frequency control device to change a pattern at high speed, it is necessary for data to be loaded into a local memory which can be read out at high speed. However, on the other hand, it is necessary to store a large amount of data, therefore it is necessary to secure a large capacity of local memory. Consequently, there is a problem such that memory which can read out at high speed is expensive in comparison with a HDD (Hard Disc Drive) which can secure the same capacity. Further, in a case where a volatile memory such as RAM (Random Access Memory) is used as a local memory, when data of a memory is lost by cutting off from the circuit caused by trouble, etc., it takes a long time to redownload data or recover data. Further, in order to prevent misirradiation, it is necessary to change a pattern at high speed without error, however, in a case where data is sent through a host computer in a conventional way, processing time is increased accordingly. Consequently, there is a case to which a scanning irradiation method cannot be applied.

This invention is made so as to solve the above-mentioned problems, and aims to provide a high-frequency control device which can perform a scanning irradiation method with less amount of local memory capacity.

Means for Solving the Problems

This invention provides a high-frequency control device for an accelerator for controlling a high-frequency to be applied to an acceleration cavity of an accelerator which generates a particle beam to be used for a particle beam therapy, wherein a hard disk drive memory which stores pattern data of a high-frequency to be applied for each combination of energy and intensity of the generated particle beam; and a local memory, which reads a plurality of pattern data of a high-frequency for each patient together with the sequential order of changing energy and intensity from the hard disk drive memory and stores data in order to perform a scanning irradiation method in which a layered particle beam irradiation region in a depth direction of an affected part of the patient is formed sequentially by changing energy and intensity of the particle beam sequentially to irradiate an affected part of a patient which is an irradiation subject with the particle beam, and which reads out data faster than the hard disk drive memory are provided.

Advantage of the Invention

According to a high-frequency control device of this invention, a high-frequency control device, which can perform a scanning irradiation method with less amount of local memory capacity, can be provided.

BRIEF DESCRIPTION OF THE DRAWINGS

FIG. 4 is a chart describing an irradiation procedure of scanning irradiation method in a particle beam therapy.

EMBODIMENTS FOR CARRYING OUT THE INVENTION

Embodiment 1

Figure 1:
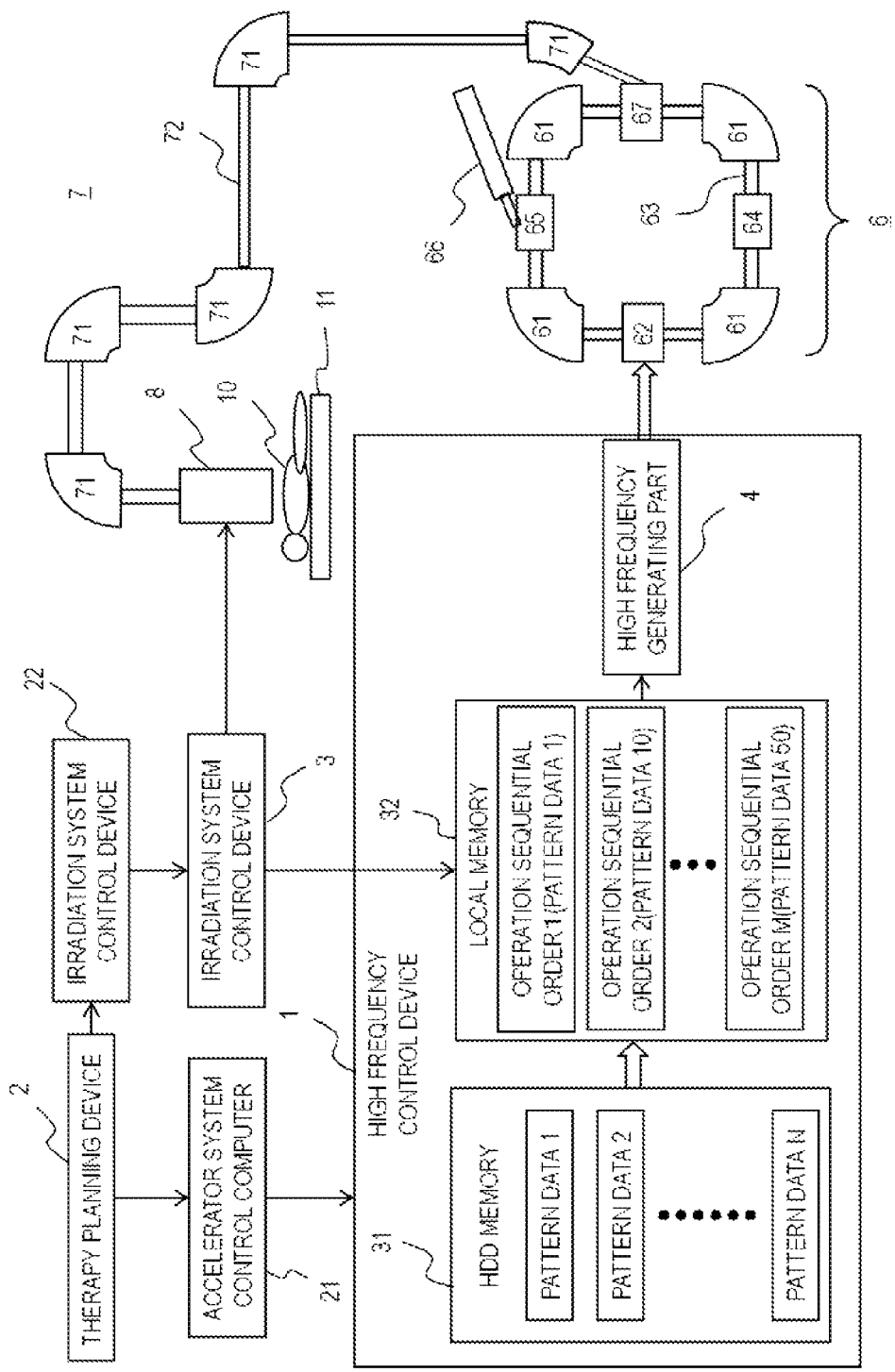
FIG. 1 is a block diagram showing the configuration of a high-frequency control device according to Embodiment 1 of this invention.
Figure 2:
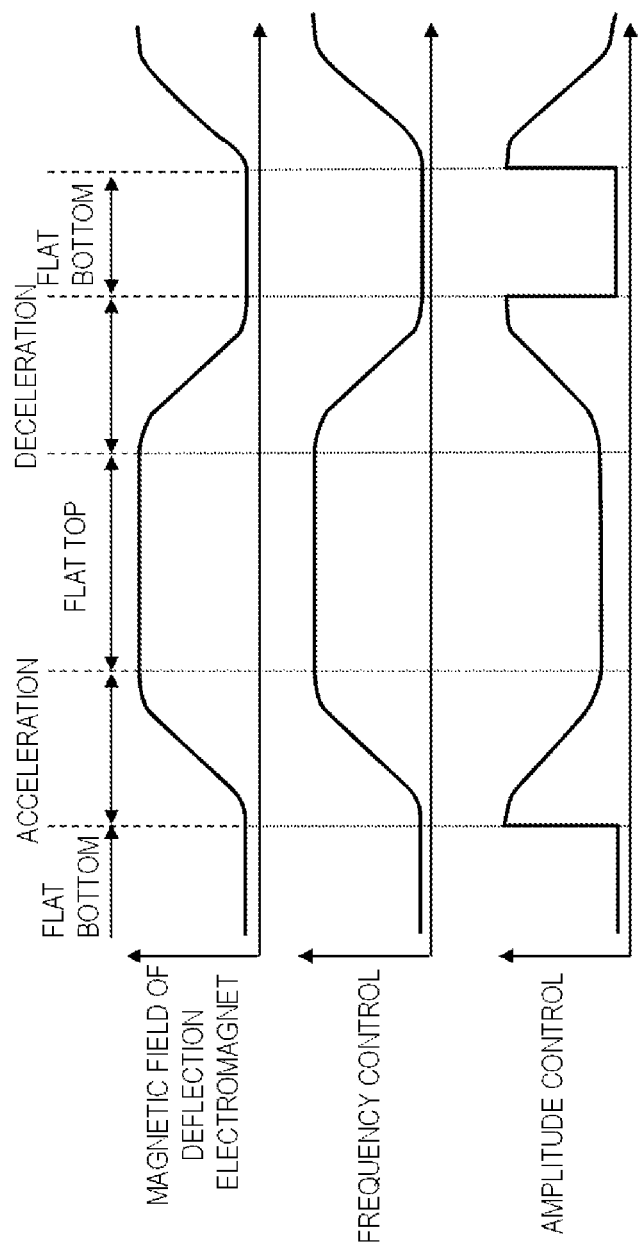
FIG. 2 is a diagram describing control patterns of a high-frequency at an acceleration cycle of control of a high-frequency control device according to Embodiment 1 of this invention.

Hereinafter, the configuration of a high-frequency control device according to Embodiment 1 will be described. FIGS. 1 to 5 are drawings describing a high-frequency control device according to Embodiment 1 of this invention. FIG. 1 is a block diagram describing a principal configuration of a high-frequency control device, and an outline of whole of a particle beam irradiation therapy system including an accelerator and a particle beam irradiation device, and FIG. 2 is a diagram describing an acceleration cycle of an accelerator.

As shown in FIG. 1, a high-frequency control device 1 is a device for controlling a frequency or output of a high-frequency to be applied to an acceleration cavity 62, which is a main component, in an circular accelerator 6 (hereinafter will be referred to as an accelerator 6) such as a synchrotron. In order to store data for controlling a high-frequency generating part 4, the high-frequency control device 1 has a HDD (Hard Disk Drive) memory 31 and a local memory 32 such as RAM, etc. which can read data at higher speed than a HDD memory.

First, an outline of the accelerator 6 will be described using a synchrotron as an example of an accelerator. The accelerator 6 comprises deflection electromagnets 61 for forming an orbit, an acceleration cavity 62 for accelerating a particle beam using a high-frequency and vacuum ducts 63 which are passages for a particle beam to pass through. In addition to the above-mentioned, the accelerator 6 comprises a prestage accelerator 66 which accelerates a charged particle beam in advance, an injector 65 which injects charged particles, which is accelerated by the prestage accelerator 66, into the accelerator 6, a beam monitor 64 for monitoring a position, etc. of a particle beam which is made by gathering charged particles to have a beam-shape, an extractor 67 for sending a particle beam from the accelerator 6 to a particle beam transport system 7 comprising transport system deflection electromagnets 71, vacuum ducts 72, etc. A particle beam which is transported by the particle beam transport system 7 is irradiated from a particle beam irradiation device 8 onto an affected part of a patient 10, which is an irradiation subject, on a therapy table 11. It is necessary for an operation of the particle beam irradiation device 8 to cooperate with an operation of the accelerator 6. A control signal for cooperating operation, for example, is outputted by an irradiation system control device 3 to the particle beam irradiation device 8 and the high-frequency control device 1.

A particle beam is accelerated to be a predetermined energy in the accelerator 6. In order to accelerate a particle beam to be a predetermined energy, it is necessary to change a frequency and amplitude of a high-frequency to be applied to an acceleration cavity 62 while changing magnetic field intensity of deflection electromagnets 61 of the accelerator. FIG. 2 shows one example of the above-mentioned change. As shown in the uppermost stage in FIG. 2, a magnetic field of the deflection electromagnet 61 of the accelerator 6, that is, a deflection magnetic field is changed according to a definite pattern. At this time, an orbit frequency of a particle beam is changed, therefore, in order to accelerate a particle beam stably, as shown in the second stage and the third stage in FIG. 2, regarding a high-frequency signal which is applied to the acceleration cavity 62, it is necessary to control a frequency and amplitude according to a predetermined pattern.

Hereinafter, an outline of an operation of an accelerator from acceleration to extraction will be described. First, the state of the minimum level of energy is called a flat bottom. In the flat bottom, a beam is injected from the prestage accelerator 66 and is accumulated in a synchrotron. Next, a high-frequency signal which is an OFF-state is turned ON, and by increasing a voltage, charged particles are captured so as for the charged particles to be gathered at a same phase.

Next in an acceleration period, based on magnetic variation of electromagnets, a beam is accelerated by controlling a frequency and amplitude of a high-frequency signal. In a case where excitation change speed of a magnetic field is mostly constant, a start part and an end part are referred to as smoothing distinctively.

Next, at a point when a beam reaches to a predetermined energy, acceleration is terminated and the states enters a flat top state where a magnetic field does not change. In the flat top stage, in order to make a condition which is suitable for extracting a beam from a synchrotron, fine adjustments of amplitude, a frequency, etc. of a high-frequency signal are made. For the duration of a flat top, on demand of users of a beam, a beam is extracted out of a synchrotron. Next, after the lapse of a predetermined time, or at a point when a beam is used up, preparation for decreasing a magnetic field of a synchrotron is made.

Next is a deceleration period, and during the deceleration period, a magnetic field of a synchrotron is reduced to be a minimum level. The synchrotron restores the condition to be a flat bottom state, and makes an electric power restore to be an initial state. The above-mentioned cycle of an operation pattern is referred to as an acceleration cycle.

In response to a flat bottom period, an acceleration period, a flat top period and a deceleration period which show the change of a deflection magnetic field of the accelerator 6, a frequency and amplitude of a high-frequency which is applied to the acceleration cavity 62 is changed as shown in the second stage and the third stage in FIG. 2. A pattern of variation of a deflection magnetic field and a high-frequency is determined by a combination of energy and intensity.

Pattern data for controlling a high-frequency signal of operation pattern in combination of energy and intensity is stored in the HDD memory 31. In a case of scanning irradiation method, for example, there are 60 kinds of energy, and per each energy, there are eight levels of intensity, that is, there are 480 kinds of operation pattern which is obtained by a numerical formula 60×8=480. Regarding each operation pattern, it is necessary to store control data of a high-frequency signal for driving the acceleration cavity 62 which corresponds to a flat bottom period, an acceleration period, a flat top period and a deceleration period as pattern data. Regarding each pattern data, each combination of energy and intensity is stored in the HDD memory 31, that is, for example, in pattern data 1, energy is 400 MeV and intensity is 1, and in patter data 2, energy is 400 MeV and intensity is 2.

Figure 3:
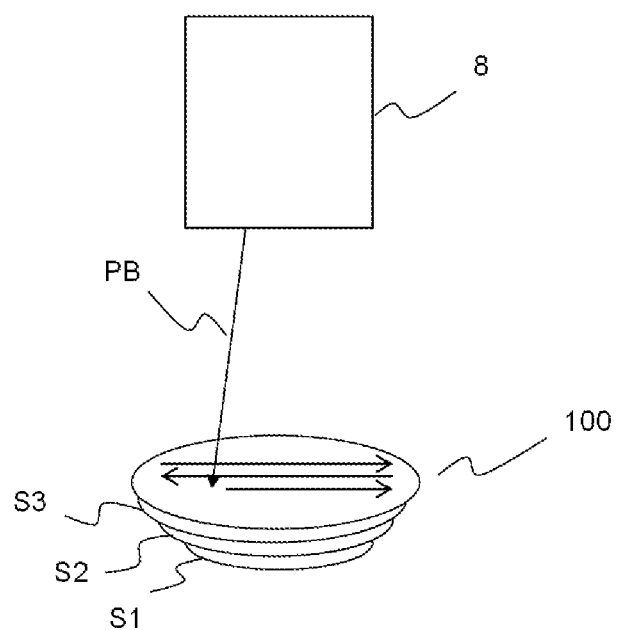
FIG. 3 is a drawing describing a scanning irradiation method in a particle beam therapy.

FIG. 3 shows an image in which a particle beam is irradiated onto an affected part 100 of a patient 10 according to a scanning irradiation method. A thin pencil-shaped particle beam PB is scanned laterally by the particle beam irradiation device 8 so as to irradiate the affected part 100. At this time, in a moving direction of a particle beam PB, that is, in a depth direction, a part of maximum absorption depth of a particle beam which is referred to as Bragg Peak which is determined by energy of a particle beam is irradiated. Accordingly, by changing energy of a particle beam, an irradiation position in a depth direction can be changed. That is, by scanning a particle beam having a certain level of energy laterally, a part in a depth direction which corresponds to the energy is irradiated. Consequently, by scanning a particle beam having a certain level of energy to irradiate, a layered part is irradiated. Next, by changing energy so as to scan a particle beam PB laterally, a layered part having a different depth can be irradiated.

When a level of energy of a particle is high, a Bragg Peak is formed in a deep part. First, by scanning a particle beam PB having a predetermined high level of energy is scanned laterally, a layered region which is indicated by S1 in FIG. 3 is irradiated. Next, by decreasing a level of energy of a particle beam, a layered region which is indicated by S2 is irradiated. By decreasing further a level of energy of a particle beam, a layered region which is indicated by S3 can be irradiated. In the above-mentioned way, a layered region having a different depth can be irradiated by changing energy. By combining energy change and scanning in a lateral direction, a particle beam can be irradiated in a three-dimensional affected region.

For each patient, what kinds of irradiation will be applied, that is, an irradiation procedure, is determined based on a therapy plan. This irradiation procedure is sent from a therapy planning device 2 to an accelerator system control computer 21 and an irradiation system control computer 22, after each computer stores the irradiation procedure, and then the irradiation procedure is sent to the high-frequency control device 1 and the irradiation system control device 3. Information regarding an irradiation procedure includes energy and intensity of a particle beam to be irradiated. FIG. 4 shows an example of a combination of energy and intensity of particle beam for each irradiation. First, a particle beam having energy 400 MeV and intensity 3 is irradiated. That is, a part having a depth which corresponds to energy 400 MeV is irradiated in a layer shape. Secondary, a particle beam having energy 380 MeV and intensity 3 is irradiated. That is, a part which is shallower than a part which was irradiated firstly is irradiated in a layer shape. In the above-mentioned way, by decreasing energy of a particle beam sequentially, a part to be irradiated is made shallow so as to irradiate whole of an affected part.

Figure 5:
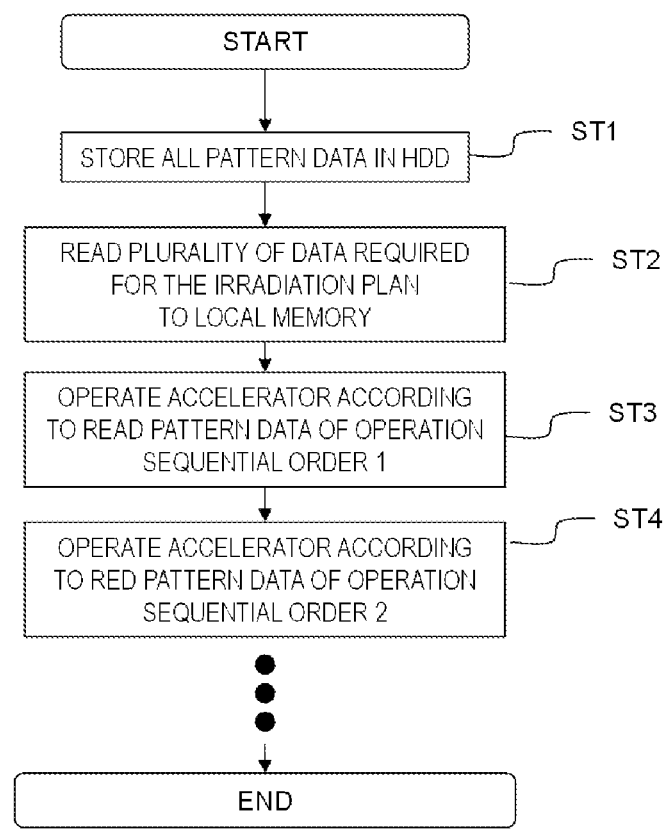
FIG. 5 is a flow chart describing an operation of a high-frequency control device according to Embodiment 1 of this invention.
Figure 6:
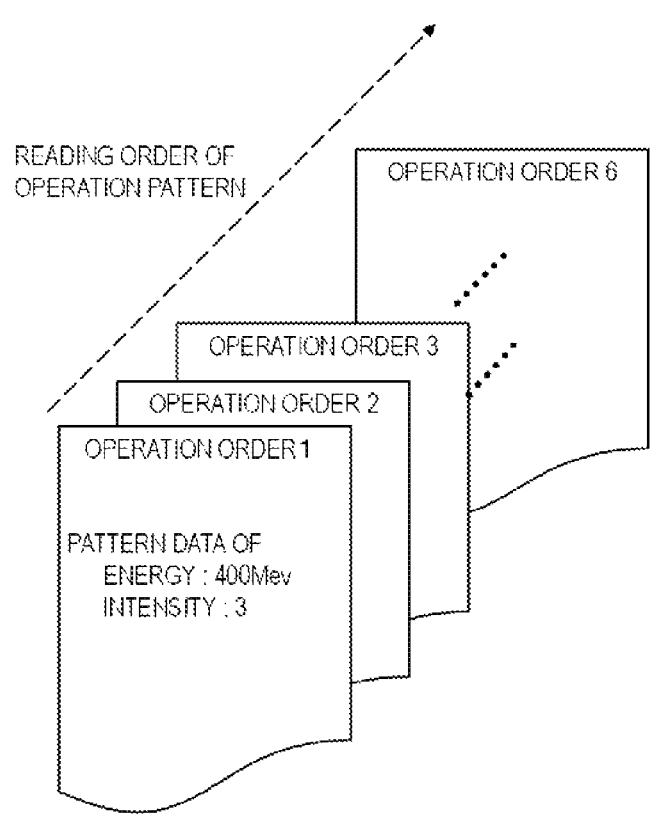
FIG. 6 is a chart showing one example of data organization which is stored in a local memory of a high-frequency control device according to Embodiment 1 of this invention.

A flow to perform the above-mentioned irradiation will be described referring to a flow diagram in FIG. 5. As a preliminary stage, all of pattern data corresponding to a combination of all energy and all intensity is sent from the accelerator system control computer 21 to the HDD memory 31 and is stored (ST1). Before irradiating a patient with a particle beam, based on an irradiation procedure according to a therapy plan of the patient, a plurality of data which is required is read from the HDD memory 31 together with a sequential order of irradiation (a sequential order of operation) to the local memory 32 (ST2). FIG. 6 shows an image of an example of organization of pattern data which is read. In the local memory 32, pattern data, that is, information regarding a high-frequency control is stored according to operation sequential order.

By completing the above-mentioned procedure, preparation for irradiation is completed. When a particle beam is irradiated, a control signal for irradiation is sent from the irradiation system control device 3 to the high-frequency control device 1 or the particle beam irradiation system 8. First, when a signal for starting irradiation is sent from the irradiation system control device 3, the high-frequency generating part 4 starts to generate a high-frequency according to pattern data of an operation sequential order 1 which is stored in the local memory 32, and a particle beam is accelerated by the accelerator 6 (ST3). At a moment when energy reaches to a predetermined level, that is, at a predetermined timing of a flat top period shown in FIG. 2, a particle beam starts to be extracted, in synchrony with that, a particle beam is scanned laterally by the particle beam irradiation system 8. After irradiation of energy according to an operation sequential order 1 is completed, the accelerator 6 prepares for following acceleration in order to perform irradiation according to an operation sequential order 2. When a signal of starting irradiation according to an operation sequential order 2 is sent from the irradiation system control device 3, according to pattern data of operation sequential order 2 which is stored in the local memory 32, the high-frequency generating part 4 starts to generate a high-frequency and a particle beam is accelerated by the accelerator 6 (ST4). At a moment when energy reaches to a predetermined level, that is, at a predetermined timing of a flat top period shown in FIG. 2, a particle beam starts to be extracted, in synchrony with that, a particle beam is scanned laterally by the particle beam irradiation system 8. As above-mentioned, energy and intensity is changed according to a therapy plan for each operation sequential order, a layered region in an affected part is irradiated for each energy so as to irradiate whole of an affected part.

As above mentioned, according to a high-frequency control device in EMBODIMENT 1, from a large amount of pattern data which is stored in the HDD memory 31, pattern data of operation sequential order according to a therapy plan for each patient is read to the local memory 32 which can read data at high speed. According to the high-frequency control device, the high-frequency generating part 4 is controlled by pattern data which is stored in the local memory 32 according to a control signal which is sent from the irradiation system control device 3. Consequently, in comparison with an operation which is performed by reading pattern data from the HDD memory 31 to the local memory 32 for each operation, controlling can be performed at higher speed. Further, in comparison with a case where a HDD memory is not provided and a large amount of pattern data is stored in a local memory, only a small capacity of local memory is required, therefore, configuration of the high-frequency control device is simple.

Embodiment 2

Figure 7:
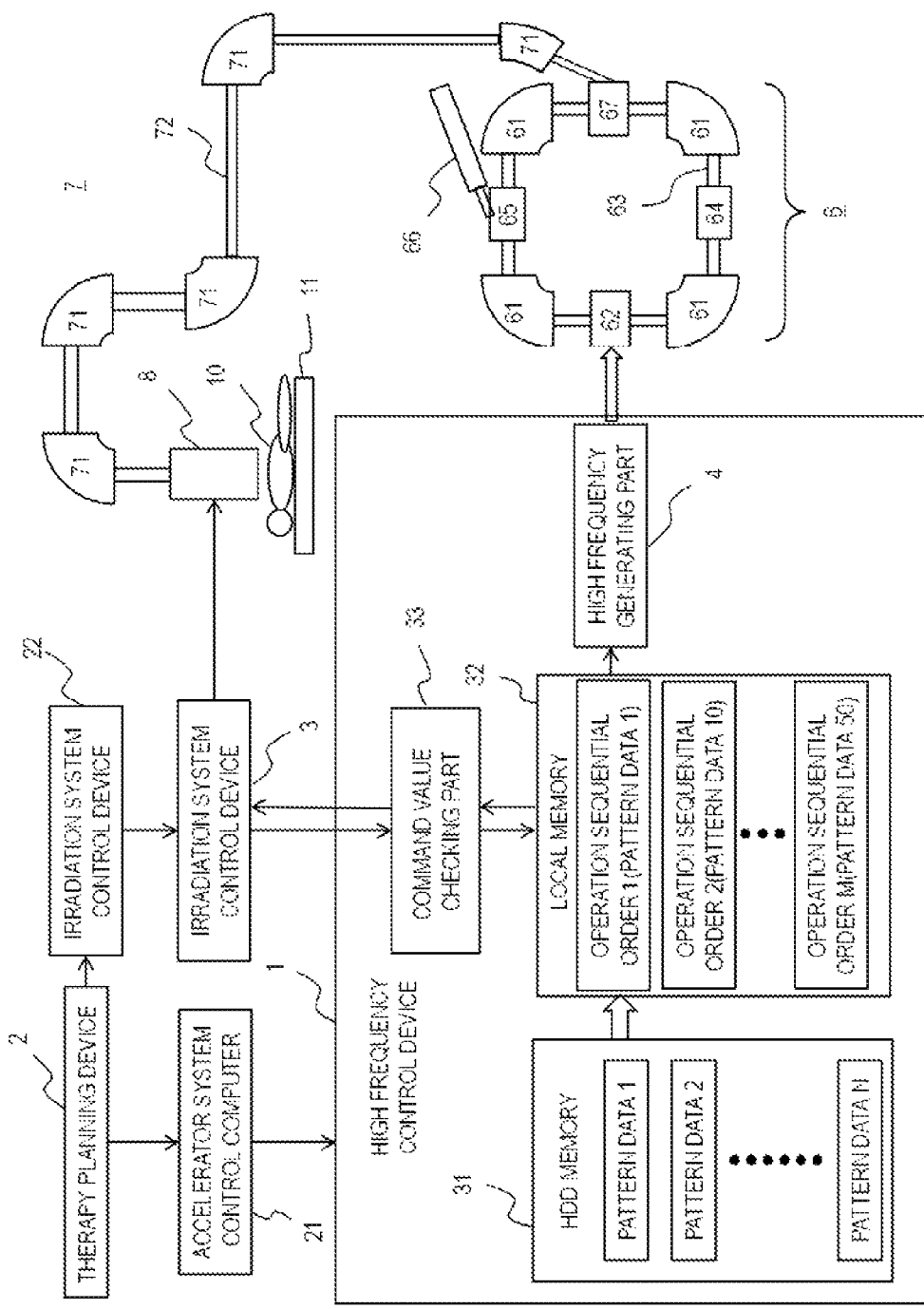
FIG. 7 is a block diagram showing a configuration of a high-frequency control device according to Embodiment 2 and Embodiment 3 of this invention.

FIG. 7 is a block diagram describing the configuration of a high-frequency control device including an accelerator according to Embodiment 2 of this invention. In FIG. 7, a reference character which is same as that in FIG. 1 shows a same part or an equivalent part. In EMBODIMENT 2, in addition to a high-frequency control device according to EMBODIMENT 1, a command value checking part 33 is provided. In this invention, for each patient, pattern data is read from a HDD memory 31 and is stored in a local memory 32. When an irradiation is performed, from the local memory 32, pattern data which is stored, that is, information regarding a high-frequency is sent successively to a high-frequency generating part 4 according to a command from an irradiation system control device 3. In the command value checking part 33, data to be sent out is checked whether it is correct or not.

Figure 8:
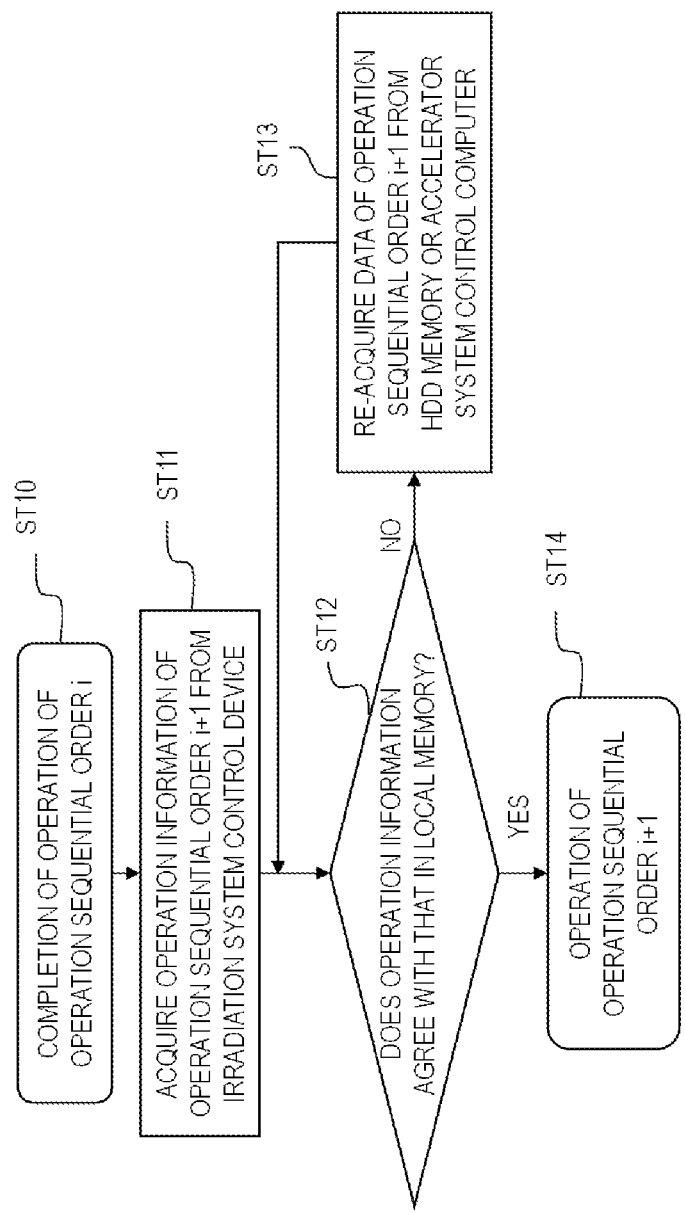
FIG. 8 is a flow chart describing an operation of a high-frequency control device according to Embodiment 2 of this invention.

A checking procedure in the command value checking part 33 will be described referring to a flow chart in FIG. 8. For example, at a point of time when an operation of operation sequential order i is completed (ST10), operation information of subsequent operation of operation sequential order i+1, that is, combination of energy and intensity will be sent from the irradiation system control device 3 to the command value checking part (ST11). Whether the above-mentioned operation information agrees with operation information regarding the operation of operation sequential order i+1 which is stored in the local memory 32 or not will be checked (ST12). In a case where the agreement is confirmed (ST12 YES), an operation of operation sequential order i+1 starts according to pattern data of operation sequential order i+1 which is stored in the local memory 32. In a case where the agreement is not confirmed (ST12 NO), an operation of operation sequential order i+1 does not start, and for example, pattern data of re-operation sequential order i+1 is acquired from the HDD memory 32 (ST13). After that, a checking procedure of ST12 is performed again. In a case where the agreement is not confirmed again, pattern data of operation sequential order i+1 is directly acquired from an accelerator system control computer 21 (ST13). In the above-mentioned way, until an operation information which is obtained from the irradiation system control device 3 agrees with an operation information in the local memory 32, data acquisition is continued.

As above-mentioned, in EMBODIMENT 2, the command value checking part 33 is provided, by checking whether a command value agrees with data in the local memory 32, an operation according to incorrect data can be prevented.

Embodiment 3

Figure 9:
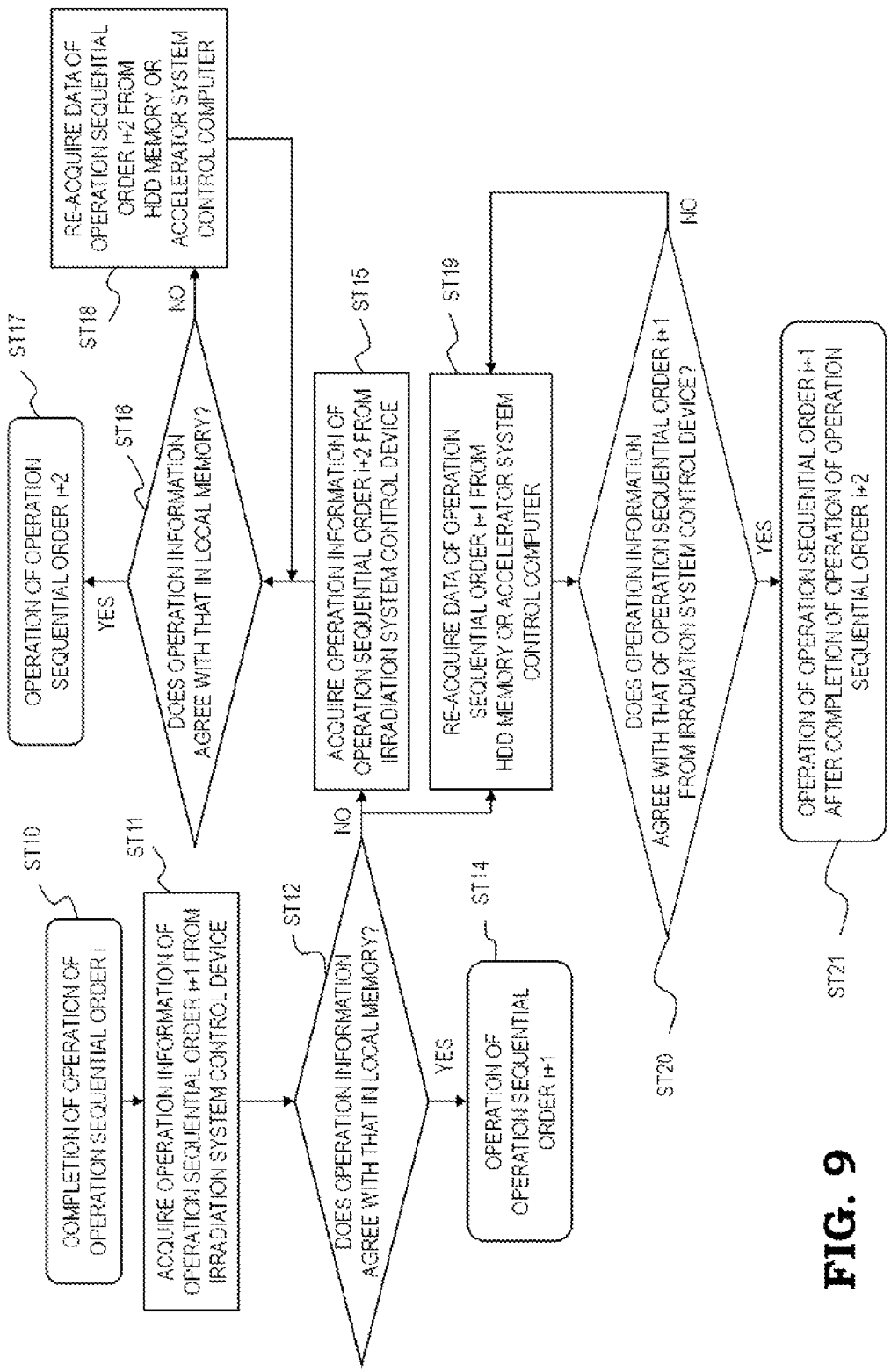
FIG. 9 is a flow chart describing an operation of a high-frequency control device according to Embodiment 3 of this invention.

FIG. 9 is a flow chart showing an operation procedure of a high-frequency control device according to EMBODIMENT 3. The configuration of a high-frequency device 1 is same as that shown in FIG. 7. In a command value checking part 33, data which is sent by the high-frequency device 1 is checked whether it is correct or not. In a case where operation information of operation sequential order i+1 which is acquired from an irradiation system control device 3 in step ST12 does not agree with operation information of operation sequential order i+1 (ST12 NO), first, operation information of subsequent operation sequential order i+2 is acquired from the irradiation system control device (ST15), and operation information is compared with operation information of operation sequential order i+2 which is stored in a local memory 32 (ST16). In a case where both of the operation information is in agreement (ST16 YES), an operation of operation sequential order i+1 is omitted, and an operation of operation sequential order i+2 is performed (ST17). On the other hand, data of operation sequential order i+1 is acquired again from a HDD memory 31 while an operation of operation sequential order i+2 is performed (ST19). When it is checked such that data of operation sequential order i+1 in a local memory agrees with data from an irradiation control device (ST20 YES), after an operation of operation sequential order i+2 is completed, an operation of operation sequential order i+1 is performed (ST21).

In a case where data is not in agreement in ST16 (ST16 NO), an operation of operation sequential order i+2 is not started, for example, pattern data of operation sequential order i+2 is acquired from the HDD memory 31 again (ST18). In this case, when data of operation sequential order i+3 is checked at the same time, and it is checked such that data of operation sequential order i+3 is correct, an operation of operation sequential order i+3 may be performed while data of operation sequential order i+1 and operation sequential order i+2 is acquired again.

As above mentioned, changing operation sequential order will not make any problem for a particle beam therapy. In a particle beam therapy, irradiation may be performed so as for an integrated irradiation dose in each irradiation site to reach to a planned value. Consequently, any irradiation sequential order is acceptable, that is, any irradiation sequential order of each irradiation layer indicated by S1, S2 and S3 shown in FIG. 2 is acceptable. That is, after the S1 layer is irradiated, the S3 layer may be irradiated and the S2 layer may be irradiated at the end. Consequently, in a scanning irradiation method, without irradiating according to energy sequential order which is planned in a therapy plan, and irradiation sequential order may be changed. In a case where it takes long time to check data in a memory, as in the above-mentioned, by performing a procedure so as for data in a memory to be correct data while an operation of other operation sequential order is performed, without increasing whole of irradiation time, an integrated irradiation dose according to a therapy plan can be applied to an irradiation site, that is, an affected part

REFERENCE CHARACTERS 1. high-frequency control device
2. therapy planning device
3. irradiation system control device
4. high-frequency generating part
6. circular accelerator (accelerator)
7. particle beam transport system
8. particle beam irradiation system
10. patient
21. accelerator system control computer
22. irradiation system control computer
61. deflection electromagnet
62. acceleration cavity
63. vacuum duct
64. beam monitor
65. injector
66. prestage accelerator
67. extractor
71. transport system deflection electromagnet
100. affected part

The invention claimed is:

1. A high-frequency control device for an accelerator to control a high frequency which is applied to an acceleration cavity of an accelerator which generates a particle beam to be used for a particle beam therapy, wherein the high-frequency control device for an accelerator comprises:
 a hard disk drive memory which stores pattern data of a high frequency to be applied for each combination of energy and intensity of the generated particle beam;
 a local memory, which reads a plurality of pattern data of a high frequency for each patient together with a sequential order of changing energy and intensity from the hard disk drive memory, and stores data in order to perform a scanning irradiation method in which a layered particle beam irradiation region in a depth direction of an affected part of the patient is formed sequentially by changing energy and intensity of the particle beam sequentially to irradiate the affected part of the patient which is an irradiation subject with the particle beam, and which reads out data faster than the hard disk drive memory, and
 a command value checking part which checks whether a command value from an irradiation system control device, which controls a particle beam irradiation device for irradiating the affected part which is the irradiation subject for each time when energy and intensity of the particle beam is changed, is in agreement with pattern data which is sent out from the local memory or not,
 wherein in a case where it is judged that a command value from the irradiation system control device is not in agreement with pattern data which is sent out from the local memory, the accelerator is operated according to subsequent pattern data of energy and intensity, and during the operation, data in the local memory is reread until the data pattern is in agreement with the command value.

2. A particle beam therapy system comprising the accelerator, a particle beam transportation system which transports a particle beam which is extracted from the accelerator, and a particle beam irradiation device for irradiating the particle beam which is transported onto the irradiation subject,
 wherein a high frequency which is applied to the acceleration cavity of the accelerator is controlled by a high-frequency control device according to claim 1.

* * * * *